United States Patent [19]

Bruns, Jr. et al.

[11] Patent Number: 5,663,192
[45] Date of Patent: Sep. 2, 1997

[54] HETEROCYCLIC NEUROPEPTIDE Y RECEPTOR ANTAGONISTS

[75] Inventors: Robert F. Bruns, Jr., Carmel; Donald R. Gehlert, Indianapolis, both of Ind.; J. Jeffry Howbert, Bellevue, Wash.; William H. W. Lunn, Indianapolis, Ind.

[73] Assignee: Eli Lilly and Company, Indianapolis, Ind.

[21] Appl. No.: 326,413

[22] Filed: Oct. 20, 1994

[51] Int. Cl.⁶ .......................... A61K 31/40; A61K 31/38; A61K 31/34

[52] U.S. Cl. .................. 514/420; 514/418; 514/448; 514/470

[58] Field of Search ..................... 514/419, 420, 514/448, 470

Primary Examiner—Theodore J. Criares
Attorney, Agent, or Firm—Paul J. Gaylo; David E. Boone

[57] ABSTRACT

This invention provides methods for treating or preventing a condition associated with an excess of neuropeptide Y which methods comprise administration of one or more substituted benzofurans, benzothiophenes or indoles.

23 Claims, No Drawings

HETEROCYCLIC NEUROPEPTIDE Y RECEPTOR ANTAGONISTS

BACKGROUND OF THE INVENTION

Neuropeptide Y is a peptide present in the central and peripheral nervous systems. The peptide co-exists with noradrenaline in many neurons and acts as a neurotransmitter per se or synergistically together with noradrenaline. Neuropeptide Y-containing fibers are numerous around arteries in the heart, but are also found around the arteries in the respiratory tract, the gastrointestinal tract, and the genitourinary tract. Neuropeptide Y is also present in the cerebrum with effects on blood pressure, feeding, and the release of different hormones. Alterations in central concentrations of neuropeptide Y have been implicated in the etiology of psychiatric disorders.

Neuropeptide Y was discovered, isolated and sequenced about ten years ago from porcine brain as part of a general screening protocol to discover carboxy-terminal amidated peptides and was named neuropeptide Y due to its isolation form neural tissue and the presence of tyrosine as both the amino and carboxy terminal amino acid. Neuropeptide Y is a member of the pancreatic family of peptides and shares significant sequence homology with pancreatic polypeptide, and peptide YY.

Neuropeptide Y and the other members of its family of peptides all feature a tertiary structure consisting of an N-terminal polyproline helix and an amphiphilic α-helix, connected with a β-turn, creating a hairpin-like loop, which is sometimes referred to as the pancreatic polypeptide (PP) fold. The helices are kept together by hydrophobic interactions. The amidated C-terminal end projects away from the hairpin loop.

Subsequent to its discovery neuropeptide Y was identified as being the most abundant peptide in the central nervous system with widespread distribution including the cortex, brainstem, hippocampus, hypotahlamus, amygdala, and thalamus as well as being present in the peripheral nervous system in sympathetic neurons and adrenal chromaffin cells.

Neuropeptide Y seems to fulfill the main neurotransmitter criteria, since it is stored in synaptic granules, is released upon electrical nerve stimulation, and acts at specific receptors. It is clear that neuropeptide Y is an important messenger in its own right, probably in the brain, where neuropeptide Y potently inhibits the activity of adenylate cyclase and induces an increase in the intracellular levels of calcium. Central injection of neuropeptide Y results in blood pressure changes, increased feeding, increased fat storage, elevated blood sugar and insulin, decreased locomotor activity, reduced body temperature, and catalepsy.

Neuropeptide Y (as well as its chemical relatives) acts upon membrane receptors that are dependent on guanine nucleotides, known as G protein-coupled receptors. G proteins are a family of membrane proteins that become activated only after binding guanosine triphosphate. Activated G proteins in turn activate an amplifier enzyme on the inner face of a membrane; the enzyme then converts precursor molecules into second messengers.

Neuropeptide Y appears to interact with a family of closely related receptors. These receptors are generally classified into several subtypes based upon the ability of different tissues and receptors to bind different fragments of neuropeptide Y and the closely related peptide YY. The Y1 receptor subtype appears to be the major vascular neuropeptide Y receptor. The Y2 receptor subtypes can also occur postjunctionally on vascular smooth muscle. The as-yet-unisolated Y3 receptor subtype appears to be neuropeptide Y-specific, not binding peptide YY. This receptor is likely to be present in the adrenal tissues, medulla, heart, and brain stem, among other areas. [For a review of neuropeptide Y and neuropeptide Y receptors, see, e.g., C. Wahlestedt and D. Reis, Annual Review of Pharmacology and Toxicology, 33:309–352 (1993)].

In view of the wide number of clinical maladies associated with an excess of neuropeptide Y, the development of neuropeptide Y receptor antagonists will serve to control these clinical conditions. The earliest such receptor antagonists were peptide derivatives. These antagonists proved to be of limited pharmaceutical utility because of their metabolic instability.

In essence, this invention provides a class of potent non-peptide neuropeptide Y receptor antagonists. By virtue of their non-peptide nature, the compounds of the present invention do not suffer from the shortcomings, in terms of metabolic instability, of known peptide-based neuropeptide Y receptor antagonists.

SUMMARY OF THE INVENTION

This invention encompasses methods for the treatment or prevention of a physiological disorder associated with an excess of neuropeptide Y, which method comprises administering to a mammal in need of said treatment an effective amount of a compound of Formula I

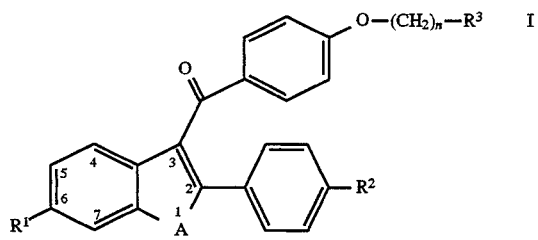

wherein:

A is —O—, —S(O)$_m$—, or —N(R$^{11}$)—;
where R$^{11}$ is hydrogen or C$_1$–C$_6$ alkyl, and
m is 0, 1, or 2;

R$^1$ is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, or trifluoromethyl;

R$^2$ is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, or trifluoromethyl;

n is 1–6;

R$^3$ is a group of the formula

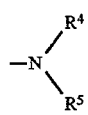

wherein R$^4$ and R$^5$ are independently C$_1$–C$_6$ alkyl or combine to form, along with the nitrogen to which they are attached, a heterocyclic ring selected from the group consisting of hexamethyleneiminyl, piperazinyl, heptamethyleneiminyl, imidazolinyl, piperidinyl, 4-methylpiperidinyl, pyrrolidinyl, or morpholinyl;

with the proviso that when n is 2 and A is —S—, $R^1$ and $R^2$ are not both selected from the group consisting of hydroxy, methoxy, and $C_2$–$C_7$ alkanoyloxy;

or a pharmaceutically acceptable salt or solvate thereof.

DETAILED DESCRIPTION AND PREFERRED EMBODIMENTS

The current invention concerns the discovery that a select group of substituted benzofurans, benzothiophenes, and indoles, those of Formula I, are useful as neuropeptide Y receptor antagonists.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the terms "$C_1$–$C_4$ alkoxy" and "$C_1$–$C_3$ alkoxy".

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_4$ alkyl".

"$C_2$–$C_7$ alkanoyloxy" represents a straight or branched alkyl chain having from one to six carbon atoms attached to a carbonyl moiety joined through an oxygen atom. Typical $C_2$–$C_7$ alkanoyloxy groups include acetoxy, propanoyloxy, isopropanoyloxy, butanoyloxy, t-butanoyloxy, pentanoyloxy, hexanoyloxy, 3-methylpentanoyloxy and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

Many of the compounds of the present invention are derivatives of benzofuran which are named and numbered according to the RING INDEX, The American Chemical Society, as follows.

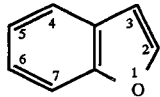

Some of the compounds of the present invention are derivatives of benzo[b]thiophene which are named and numbered according to the RING INDEX as follows.

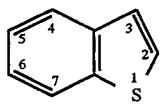

In a similar manner some of the compounds of the present invention are derivatives of indole which are named and numbered according to the RING INDEX as follows.

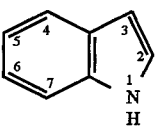

The most preferred compounds employed in the methods of this invention are those compounds of Formula I wherein a) A is —O— or —S—;

b) $R^1$ is hydrogen, hydroxy, or $C_1$–$C_3$ alkoxy;

c) $R^2$ is hydrogen, hydroxy, or $C_1$–$C_3$ alkoxy;

d) n is 1 to 3; and e) $R^3$ is piperidinyl, hexamethyleneiminyl, pyrrolidinyl, or —$NR^4R^5$, where $R^4$ and $R^5$ are $C_1$–$C_4$ alkyl.

The compounds of the instant invention as well as the compounds employed in the methods of the instant invention were made essentially as described in U.S. Pat. Nos. 4,133,814, issued Jan. 9, 1979, 4,418,068, issued Nov. 29, 1983, and 4,380,635, issued Apr. 19, 1983, all of which are herein incorporated by reference. This process provides a convenient process which acylates a methylated starting compound and then optionally demethylates it to obtain the desired dihydroxy product. The acylation and demethylation may be performed in successive steps in a single reaction mixture or the intermediate may be isolated and the demethylation step be performed in a separate reaction.

The methyl-protected compound of Formula III

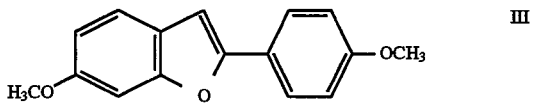

III is most easily obtained by reacting 3-methoxyphenol and α-bromo-4-methoxyacetophenone in the presence of a strong base at a relatively low temperature, to form α-(3-methoxyphenoxy)-4-methoxyacetophenone, which is then ring closed with an agent such as polyphosphoric acid at a high temperature to obtain the intermediate compound of Formula III.

The acylation of this invention is a Friedel-Crafts acylation, and is carried out in the usual way, using aluminum chloride or bromide, preferably the chloride, as the acylation catalyst.

The acylation is ordinarily carried out in a solvent, and any inert organic solvent which is not significantly attacked by the conditions may be used. For example, halogenated solvents such as dichloromethane, 1,2-dichloroethane, chloroform, and the like may be used, as can aromatics such as benzene, chlorobenzene, and the like. It is preferred to use a halogenated solvent, especially dichloromethane.

It has been found that toluene is rather easily acylated under the conditions used in the Friedel-Crafts acylation, and so it is important, when toluene is used in an earlier step of the process, to remove it as completely as possible from the protected starting compound, to avoid wasting the acylating agent.

The acylations may be carried out at temperatures from about −30° C. to about 100° C., preferably at about ambient temperature, in the range of from about 15° C. to about 30° C.

The acylating agent is an active form of the appropriate benzoic acid of Formula IV

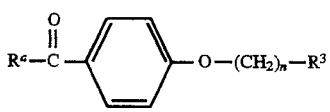

wherein R$^a$ is chloro or bromo. The preferred acylating agents are those wherein R$^a$ is chloro. Thus, the most highly preferred individual acylating agents are 4-[2-(piperidin-1-yl)ethoxy]benzoyl chloride, 4-[2-(hexamethyleneimin-1-yl)ethoxy]benzoyl chloride, 4-[2-(pyrrolidin-1-yl)ethoxy]benzoyl chloride, 4-[2-(dimethylamino)ethoxy]-benzoyl chloride, 4-[2-(diethylamino)ethoxy]benzoyl chloride, and 4-[2-(diisopropylamino)ethoxy]benzoyl chloride.

The acyl chloride used as an acylating agent may be prepared from the corresponding carboxylic acid by reaction with a typical chlorinating agent such as thionyl chloride. Care must be taken to remove any excess chlorinating agent from the acyl chloride. Most conveniently, the acyl chloride is formed in situ, and the excess chlorinating agent is distilled off under vacuum.

It is generally preferred that an equimolar amount of the compounds of Formula III and IV are reacted together. If desired, a small excess of either reactant may be added to assure the other is fully consumed. It is generally preferred to use a large excess of the acylation catalyst, such as about 2-12 moles per mole of product, preferably about 5-10 moles of catalyst per mole of product.

The acylation is rapid. Economically brief reaction times, such as from about 15 minutes to a few hours provide high yields of the acylated intermediate. Longer reaction times may be used if desired, but are not usually advantageous. As usual, the use of lower reaction temperatures call for relatively longer reaction times.

The acylation step is ended and the optional demethylation step is begun by the addition of a sulfur compound selected from the group consisting of methionine and compounds of the formula

X—S—Y wherein X is hydrogen or unbranched $C_1$–$C_4$ alkyl, and Y is $C_1$–$C_4$ alkyl or phenyl. The sulfur compounds are, preferably, the alkylthiols, such as methanethiol, ethanethiol, isopropanethiol, butanethiol, and the like; dialkyl sulfides, such as diethyl sulfide, ethyl propyl sulfide, butyl isopropyl sulfide, dimethyl sulfide, methyl ethyl sulfide, and the like; benzenethiol; methionine; and alkyl phenyl sulfides, such as methyl phenyl sulfide, ethyl phenyl sulfide, butyl phenyl sulfide, and the like.

It has been found that demethylation is most efficient when a substantial excess of the sulfur compound is used, in the range of about 4 to about 10 moles per mole of the starting benzofuran. The process may be carried out, although less efficiently, with a smaller amount of the sulfur compound (in the range of about 2 to 3 moles per mole of the starting compound). It is also possible to use a small amount of the sulfur compound, and to improve the yield by the addition of about 1 to 3 moles of an alkali metal halide, such as sodium, potassium, or lithium chloride, bromide, or iodide.

The demethylation reaction goes well at about ambient temperature, in the range of from about 15° C. to about 30° C., and such operation is preferred. The demethylation may be carried out, however, at temperatures in the range of from about –30° C. to about 50° C. if it is desired to do so. Short reaction times, in the range of about one hour, have been found to be sufficient.

After the product has been demethylated, it is recovered and isolated by conventional means. It is customary to add water to decompose the complex of the acylation catalyst. Addition of dilute aqueous acid is advantageous. The product precipitates in many instances, or may be extracted with an organic solvent according to conventional methods. The examples below further illustrate the isolation.

In an alternative process an intermediate compound of Formula V

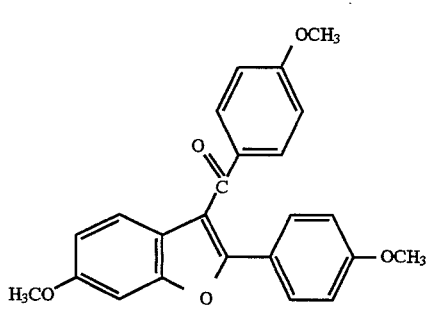

is synthesized by the reaction of 2-hydroxy-4-methoxybenzaldehyde and 1-(4-methoxyphenyl)-2-(4-methoxyphenyl)ethanone, essentially as described in Preparation 3, infra. This reaction usually employs equimolar amounts of the two reactants although other ratios are operable. The reaction is performed in a non-reactive solvent such as ethyl acetate, chloroform, and the like, in the presence of an acid. Hydrochloric acid, particularly when created by bubbling anhydrous hydrogen chloride, is an especially preferred acid. Lower alkyl alcohols are usually added to the non-polar solvent so as to retain more of the hydrochloric acid created in situ, with ethanol and methanol being especially preferred. The reaction is performed at temperatures ranging from ambient temperature up to the reflux temperature of the mixture. This reaction results in the synthesis of a compound of Formula VI

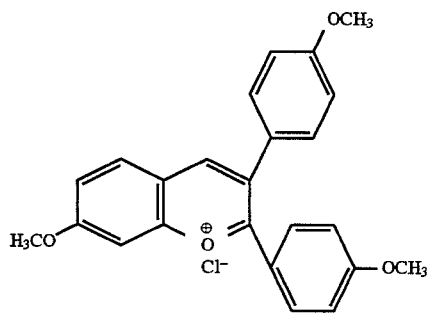

or an equivalent anion if hydrochloric acid is not used, which is then oxidized to the compound of Formula V by the addition of hydrogen peroxide. The intermediate of Formula VI may be isolated or may preferably be converted to the compound of Formula V in the same reaction vessel.

The compound of Formula V is then selectively demethylated, essentially as described in Preparation 4, infra to yield the compound of Formula VII

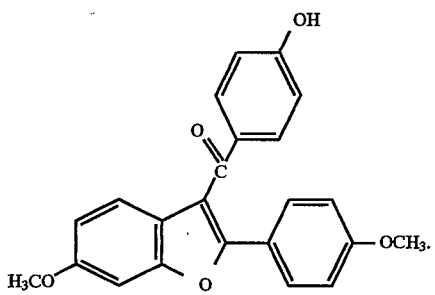

VII

The ether of the compounds of Formula I is then produced by the substitution of the hydrogen on the hydroxy group by an alkyl group, using standard means.

Those compounds of Formula I in which "A" equals —N($R^{11}$)— are prepared in essentially the same manner as the substituted benzofurans described supra. Example 15, infra, provides one such protocol for synthesizing the substituted indoles of this invention.

Those compounds of Formula I in which "A" equals —S(O)$_m$— are prepared in essentially the same manner as the substituted benzofurans described supra. The examples infra provide several exemplifications of these benzothiophenes and the oxidated derivatives thereof.

Those compounds of Formula I in which m is one or two may be prepared by oxidation of the corresponding benzothiophene in which m is zero. Oxidation may be carried out by treating the benzothiophene with an oxidizing agent, for example, m-chloroperbenzoic acid, or the like, for a time sufficient to achieve formation of the sulfoxide group. The progress of the oxidation reaction may be monitored by thin layer chromatography methods.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dicarboxylate, hexyne-1,4-dicarboxylate, caprate, caprylate, cinnamate, citrate, formate, fumarate, glycollate, heptanoate, hippurate, hydrochloride, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides and carbonates, as well as aliphatic and aromatic amines, aliphatic diamines and hydroxy alkylamines. Bases especially useful in the preparation of addition salts include ammonium hydroxide, potassium carbonate, calcium hydroxide, methylamine, diethylamine, ethylene diamine, cyclohexylamine and ethanolamine.

The pharmaceutically acceptable salts frequently have enhanced solubility characteristics compared to the compound from which they are derived, and thus are often more amenable to formulation as liquids or emulsions.

EXAMPLES

The following experiments illustrate the preparation of compounds of the invention. The terms "NMR", "IR" or "MS" following a synthesis protocol indicates that the nuclear magnetic resonance spectrum, infrared spectrum, or the mass spectrometry was performed and was consistent with the title product.

Preparation 1

Synthesis of 2-(3-methoxyphenoxy)-1-(4-methoxyphenyl)ethanone.

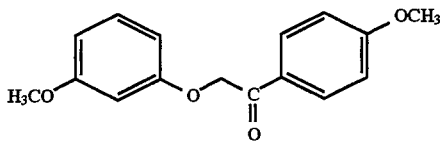

In a one liter round-bottom flask, fitted with a condenser and nitrogen inlet, were added 3-methoxyphenol (12.4 g, 0.1 mole), 4-methoxyphenacyl bromide (22.9 g, 0.1 mole), potassium carbonate (17.3 g, 0.125 mole) in 100 ml of 2-butanone. This mixture was heated to 80° C. and was maintained at this temperature for about four hours. The progress of the reaction was monitored by thin layer chromatography (silica gel, 9:1 toluene:ethyl acetate).

After the four hours at 80° C. the reaction mixture was cooled and the reaction mixture was partitioned by the addition of water. The organic phase was removed and the aqueous layer was washed with 2-butanone. The organic layers were then combined, dried over magnesium sulfate, and the solvents were removed in vacuo to yield 31.1 grams of a yellow oil. The yellow oil was further purified by chromatography, the fractions containing the desired product were then crystallized. All of the crystalline fractions were combined and then dissolved in 80 ml of hot ethanol. Fifteen milliliters of hot water was then added, the product was crystallized, and subsequently washed with an ethanol/water mixture to yield 19.1 g (70%) of the desired title product. mp 52.5°–53.5° C.

Analysis for $C_{16}H_{16}O_4$: Theory: C, 68.08; H, 5.71; N, 2.84. Found: C, 67.86; H, 5.51; N, 2.88.

Preparation 2

Synthesis of 2-methoxyphenyl-6-methoxybenzofuran.

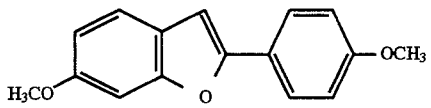

The cyclization of the product of Preparation 1 was performed essentially as described in C. Goldenberg, et al., *Chimie Therapeutique*, 398–411 (1973). In a 500 ml 3-neck round bottom flask polyphosphoric acid (30 g) was added to 200 ml of xylene. The mixture was then heated to about 120° C. To this heated mixture was then added 2-(3-methoxyphenoxy)-1-(4-methoxyphenyl)ethanone (10 g, 0.037 mole), prepared as described supra, and the temperature was raised to about 170° C., and maintained at that temperature for about eight hours. The reaction mixture was then cooled and water was added.

The dark aqueous layer was separated from the yellow organic phase. The organics were washed with water and by aqueous sodium carbonate, and then dried over anhydrous magensium sulfate. The solvents were removed in vacuo, resulting in a yellow-orange solid. The product was recrystallized from a minimum of hot acetone, followed by the addition of ethanol and water. The residual acetone was removed by boiling. Cooling to room temperature yielded white crystals (2.09 g, 22% yield). mp 158° C.

Analysis for $C_{16}H_{14}O_3$: Theory: C, 75.58; H, 5.55; O, 18.88. Found: C, 75.33; H, 5.67; O, 18.62.

Preparation 3

Synthesis of 2-(4-methoxyphenyl)-3-(4-methoxybenzoyl)-6-methoxybenzofuran

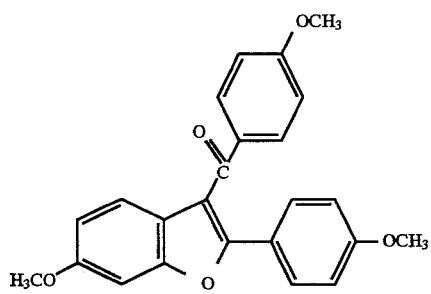

In a 250 ml 3-neck round bottom flask were added 2-hydroxy-4-methoxybenzaldehyde (10 g, 65.7 mmoles), 1-(4-methoxyphenyl)-2-(4-methoxyphenyl)ethanone (16 g, 62.6 mmoles), ethyl acetate (100 ml) and ethanol (25 ml). The reaction mixture was then warmed to about 45° C. until all the starting materials were dissolved. Hydrogen chloride gas was then bubbled in for about 30 minutes, resulting in the formation of a bright red coloration. The reaction was then allowed to stand at room temperature for about two hours at which time the solvents were removed in vacuo to leave a bright red oil.

The red oil was dissolved in 180 ml of methanol and 30 ml of 20% sulfuric acid was added with stirring and cooling. Hydrogen peroxide (30 ml) was added dropwise and the mixture was allowed to stir for about 30 minutes. A saturated sodium chloride solution (500 ml) and ethyl acetate (300 ml) were added to the reaction mixture and the organic fraction was removed. The organic layer was washed with a saturated sodium chloride solution, dried, and the solvents were removed in vacuo to provide 25 g of a reddish brown oil which was further purified by chromatography to yield the title product (1.25 g) as a yellow oil. mp 106°–109° C.

Analysis for $C_{24}H_{20}O_5$: Theory: C, 74.21; H, 5.19; O, 20.60. Found: C, 74.07; H, 5.22; O, 20.38.

Preparation 4

Synthesis of 2-(4-methoxyphenyl)-3-(4-hydroxybenzoyl)-6-methoxybenzofuran

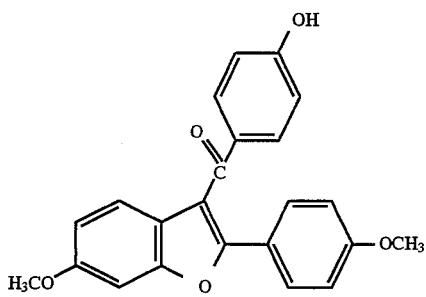

In a three-neck round bottom flask under a nitrogen atmosphere and cooled in an ice bath, ethanethiol (0.95 ml, 1.288 mmoles) was dissolved in 10 ml of anhydrous N,N-dimethylformamide. To this solution was added n-butyllithium (0.60 ml of a 1.6M in hexane solution, 0,966 mmole) followed by the addition of 2-(4-methoxyphenyl)-3-(4-methoxybenzoyl)-6-methoxybenzofuran (250 mg, 0.644 mmole), prepared as described in Preparation 3, supra. The reaction mixture was then heated to 80° C. and allowed to remain at that temperature for about 16 hours.

The reaction mixture was then poured into 1N hydrochloric acid and extracted with ethyl acetate. The organic layer was then washed with a saturated sodium chloride solution, dried over magnesium sulfate, filtered and the solvents were removed in vacuo. The desired product was further purified by column chromatography. The product was then crystallized from methanol yielding 130 mg (81%) of the desired product. mp 148°–149° C.

Analysis for $C_{23}H_{18}O_5$: Theory: C, 73.79; H, 4.85; O, 21.37. Found: C, 73.68; H, 5.12; O, 21.17.

Example 1

Synthesis of 2-(4-methoxyphenyl)-3-[4-[2-(piperidin-1-yl)ethoxy]benzoyl]-6-methoxybenzofuran

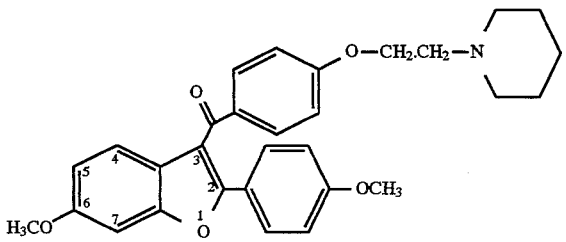

Method A: Acylation of Benzofuran

4-[2-(Piperidin-1-yl)ethoxy]benzoyl chloride (0.562 g, 1.96 mmoles) was added to ethylene chloride (20 ml), followed by the addition of 2-methoxyphenyl-6-methoxybenzofuran (0.500 g, 1.96 mmoles), prepared as described in Preparation 2, supra. This mixture was stirred at room temperature as aluminum trichloride (1.96 g, 14.7 mmoles) was added. This reaction mixture was then stirred overnight.

The reaction mixture was then poured over ice, and extracted with warm chloroform (3×50 ml). The chloroform was removed by evaporation. Sodium carbonate, water and ethyl acetate were then added and the organic layer was removed, dried over magnesium sulfate, and the solvents were removed in vacuo to provide a yellow oil. The desired product was further purified by chromatography of the yellow oil to yield the desired title product.

NMR, IR, MS.

Analysis for $C_{30}H_{31}NO_5$: Theory: C, 74.21; H, 6.44; N, 2.88; O, 16.47. Found: C, 74.11; H, 6.71; N, 2.75; O, 16.57.
Method B: Alkylation of 2-(4-methoxyphenyl)-3-(4-hydroxybenzoyl)-6-methoxybenzofuran.

In 100 ml of anhydrous N,N-dimethylformamide in a 500 ml round bottom flask were added 2-(4-methoxyphenyl)-3-(4-hydroxybenzoyl)-6-methoxybenzofuran (10.50 g, 28 mmoles), prepared as described in Preparation 4, supra, and potassium carbonate (6.20 g, 34 mmoles). This mixture was heated to 100° C. and then 2-(piperidin-1-yl)ethyl chloride (6.20 g, 34 mmoles) was added gradually. The reaction mixture was kept at 100° C. for about one hour.

The N,N-dimethylformamide was evaporated and the residue was dissolved in ethyl acetate and water. The ethyl acetate layer was removed and the aqueous layer was washed with more ethyl acetate. The organic fractions were combined, dried over magnesium sulfate, and the solvents were removed in vacuo, yielding 13.3 g of a yellow oil which crystallized upon standing. The product was recrystallized from methanol cooled to −30° C. prior to filtration, yielding 11.4 g (84%) of the desired product as pale yellow crystals. mp 87°–89° C.

Analysis for $C_{30}H_{31}NO_5$: Theory: C, 74.21; H, 6.44; N, 2.88; O, 16.47. Found: C, 74.31; H, 6.34; N, 2.63; O, 16.47.

Example 2

Synthesis of 2-(4-hydroxyphenyl)-3-[4-[2-(piperidin-1-yl)ethoxy]benzoyl]-6-hydroxybenzofuran

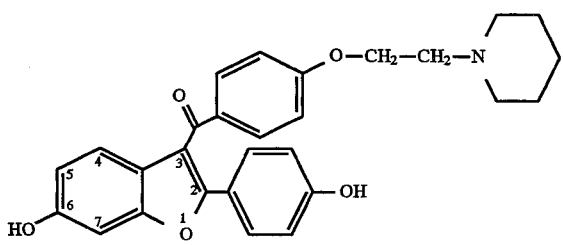

The title product was prepared by the demethylation of 2-(4-methoxyphenyl)-3-[4-[2-(piperidin-1-yl)ethoxy]benzoyl]-6-methoxybenzofuran, the product of Example 1, supra. In a 250 ml three-neck round bottom flask were combined ethylene chloride (50 ml) and aluminum trichloride (9.60 g, 72 mmoles) and ethanethiol (6.39 g, 103 mmoles) to create a pale yellow liquid. To this liquid was then added the product of Example 1 (5.00 g, 10.3 mmoles) in a gradual fashion. A red oil precipitated and the mixture was stirred for about 20 minutes. After cooling the reaction mixture in an ice bath 100 ml of tetrahydrofuran was added and the mixture was allowed to stir until all of the oil had gone into solution.

The reaction mixture was then poured over ice (200 ml) and water (500 ml) and concentrated hydrochloric acid (10 ml) were added. The oil which precipitated was separated from the liquid by decantation. The liquid was extracted with chloroform (warm, 2×300 ml). The oil was dissolved by mixing with ethyl acetate, chloroform, sodium bicarbonate, and a small amount of sodium hydroxide. The chloroform extract and the dissolved oil were transferred to separatory funnel and washed with sodium bicarbonate. The organic phase was then dried over magnesium sulfate and the solvents were removed by evaporation to yield a yellow foam, which was further purified by high performance liquid chromatography.

NMR, IR, MS.

Analysis for $C_{28}H_{27}NO_5$: Theory: C, 73.51; H, 5.95; N, 3.06. Found: C, 70.45; H, 6.34; N, 4.02.

Example 3

Synthesis of 2-(4-methoxyphenyl)-3-[4-[2-(pyrrolidin-1-yl)ethoxy]benzoyl]-6-methoxybenzofuran hydrochloride

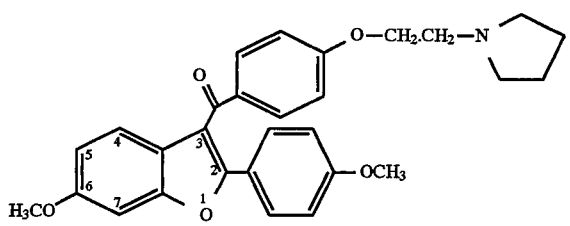

The title compound is prepared essentially as described in the process for preparing the compound of Example 1 except that 4-[2-(pyrrolidin-1-yl)ethoxy]benzoyl chloride is employed in the synthesis of Method A in place of 4-[2-(piperidin-1-yl)ethoxy]benzoyl chloride or 2-(pyrrolidin-1-yl)ethyl chloride is employed in the synthesis of Method B in place of the 2-(piperidin-1-yl)ethyl chloride.

Example 4

Synthesis of 2-(4-hydroxyphenyl)-3-[4-[2-(pyrrolidin-1-yl)ethoxy]benzoyl]-6-hydroxybenzofuran hydrochloride

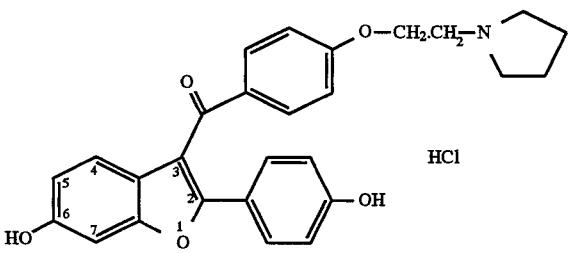

The title compound is prepared essentially as described in Example 2 except that 2-(4-methoxyphenyl)-3-[4-[2-(pyrrolidin-1-yl)ethoxy]benzoyl]-6-methoxybenzofuran is used as the starting material instead of 2-(4-methoxyphenyl)-3-[4-[2-(piperidin-1-yl)ethoxy]benzoyl]-6-methoxybenzofuran.

NMR, IR, MS.

Analysis for $C_{27}H_{26}NO_5Cl$: Theory: C, 67.57; H, 5.46; N, 2.92. Found: C, 67.84; H, 5.56; N, 2.87.

Example 5

Synthesis of 2-(4-methoxyphenyl)-3-[4-[2-(diethylamino)ethoxy]benzoyl]-6-methoxybenzofuran

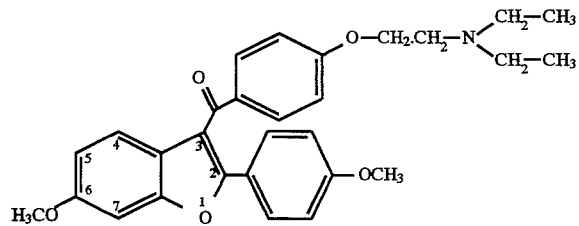

The title compound was prepared by reacting the compound of Preparation 4 supra, 2-(4-methoxyphenyl)-3-(4-hydroxybenzoyl)-6-methoxybenzofuran (10 g, 26.7 mmoles) which is dissolved in 200 ml of N,N-dimethylformamide with an equimolar amount of 2-(N,N-diethylamino)ethyl chloride (6.4 g, 32 mmoles) and potassium carbonate (11.06 g, 80.2 mmoles). The mixture was heated to 100° C. and was maintained at that temperature for about two hours. The reaction mixture was then cooled to room temperature and maintained at this temperature overnight while stirring.

The solvents were then removed by evaporation and the residue was extracted from water with ethyl acetate and washed twice with a saturated sodium chloride solution. The organic phase was dried over sodium sulfate and the solvents were removed in vacuo. The material was crystallized from hexane and recrystallized in methanol.

NMR, IR, MS.

Analysis for $C_{29}H_{31}NO_5$: Theory: C, 73.55; H, 6.60; N, 2.96. Found: C, 73.29; H, 6.50; N, 2.84.

Example 6

Synthesis of 2-(4-hydroxyphenyl)-3-[4-[2-(diethylamino)ethoxy]benzoyl]-6-hydroxybenzofuran hydrochloride

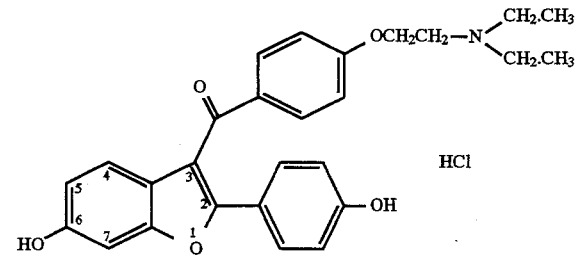

The title compound was prepared essentially as described in Example 2, supra, except that the compound of Example 5, 2-(4-methoxyphenyl)-3-[4-[2-(diethylamino)ethoxy]benzoyl]-6-methoxybenzofuran, was used as the starting material to be demethylated.

NMR, IR, MS.

Analysis for $C_{27}H_{28}NO_5Cl$: Theory: C, 67.29; H, 5.86; N, 2.91. Found: C, 67.54; H, 5.64; N, 2.92.

Example 7

Synthesis of 2-(4-methoxyphenyl)-3-[4-[2-(diisopropylamino)ethoxy]benzoyl]-6-methoxybenzofuran

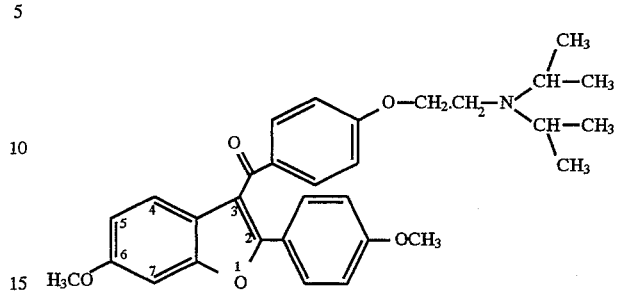

The title compound was prepared by reacting the compound of Preparation 4 supra, 2-(4-methoxyphenyl)-3-(4-hydroxybenzoyl)-6-methoxybenzofuran (10 g, 26.7 mmoles) which is dissolved in 200 ml of N,N-dimethylformamide with 2-(N,N-diisopropylamino)ethyl chloride (6.4 g, 32 mmoles) and potassium carbonate (11.06 g, 80.2 mmoles). The mixture was heated to 100° C. and was maintained at that temperature for about two hours. The reaction mixture was then cooled to room temperature and maintained at this temperature overnight while stirring.

The solvents were then removed by evaporation and the residue was extracted from water with ethyl acetate and washed twice with a saturated sodium chloride solution. The organic phase was dried over sodium sulfate and the solvents were removed in vacuo. The material was crystallized from hexane and recrystallized in methanol.

NMR, IR, MS.

Analysis for $C_{33}H_{39}NO_5$: Theory: C, 74.83; H, 7.42; N, 2.64. Found: C, 74.68; H, 7.14; N, 2.76.

Example 8

Synthesis of 2-(4-hydroxyphenyl)-3-[4-[2-(diisopropylamino)ethoxy]benzoyl]-6-hydroxybenzofuran hydrochloride

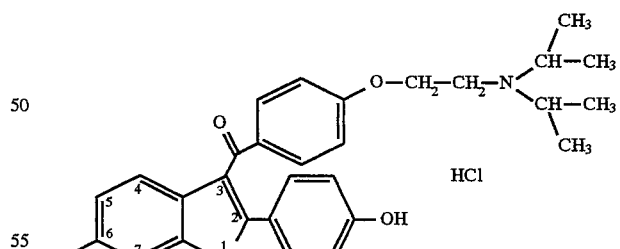

The title compound was prepared essentially as described in Example 2, supra, except that the compound of Example 7, 2-(4-methoxyphenyl)-3-[4-[2-(diispropylamino)ethoxy]benzoyl]-6-methoxybenzofuran, was used as the starting material to be demethylated.

NMR, IR, MS.

Analysis for $C_{29}H_{32}NO_5Cl$: Theory: C, 68.29; H, 6.32; N, 2.75. Found: C, 68.53; H, 6.49; N, 2.74.

Example 9

Synthesis of 2-(4-methoxyphenyl)-3-[4-[2-(dimethylamino)ethoxy]benzoyl]-6-methoxybenzofuran

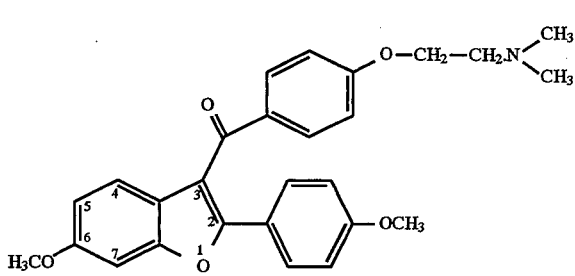

The title compound was prepared essentially as described in Example 7, supra, except that 2-(N,N-dimethylamino)ethyl chloride was reacted with 2-(4-methoxyphenyl)-3-(4-hydroxybenzoyl)-6-methoxybenzofuran instead of the 2-(N,N-diisopropylamino)ethyl chloride employed in that example.

NMR, IR, MS.

Analysis for $C_{27}H_{27}NO_5$: Theory: C, 72.79; H, 6.11; N, 3.14. Found: C, 72.51; H, 6.27; N, 3.10.

Example 10

Synthesis of 2-(4-hydroxyphenyl)-3-[4-[2-(dimethylamino)ethoxy]benzoyl]-6-hydroxybenzofuran

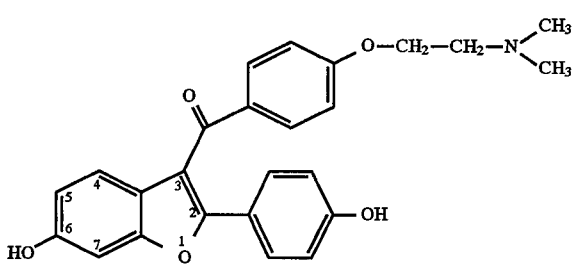

The title compound was prepared essentially as described in Example 2, supra, except that the compound of Example 9, 2-(4-methoxyphenyl)-3-[4-[2-(dimethylamino)ethoxy]benzoyl]-6-methoxybenzofuran, was used as the starting material to be demethylated.

NMR, IR, MS.

Analysis for $C_{25}H_{23}NO_5$: Theory: C, 71.93; H, 5.55; N, 3.36. Found: C, 70.69; H, 5.51; N, 3.16.

Example 11

Synthesis of 2-(4-methoxyphenyl)-3-[4-[2-(hexamethyleneimin-1-yl)ethoxy]benzoyl]-6-methoxybenzofuran

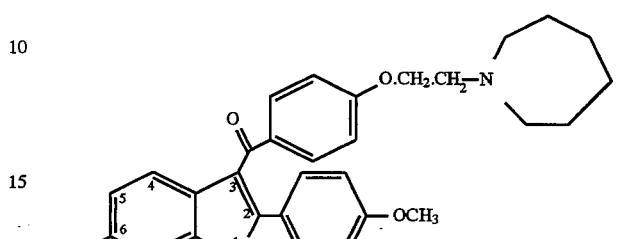

The title compound was prepared essentially as described in Example 7, supra, except that 2-(hexamethyleneimin-1-yl)ethyl chloride was reacted with 2-(4-methoxyphenyl)-3-(4-hydroxybenzoyl)-6-methoxybenzofuran instead of the 2-(N,N-diisopropylamino)ethyl chloride employed in that example.

NMR, IR, MS.

Analysis for $C_{31}H_{33}NO_5$: Theory: C, 74.53; H, 6.66; N, 2.80. Found: C, 74.69; H, 6.70; N, 2.75.

Example 12

Synthesis of 2-(4-hydroxyphenyl)-3-[4-[2-(hexamethyleneimin-1-yl)ethoxy]benzoyl]-6-hydroxybenzofuran hydrochloride

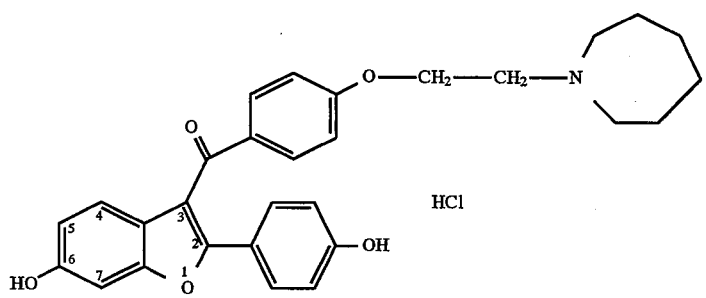

The title compound was prepared essentially as described in Example 2, supra, except that the compound of Example 11, 2-(4-methoxyphenyl)-3-[4-[2-(hexamethyleneimin-1-yl)ethoxy]benzoyl]-6-methoxybenzofuran, was used as the starting material to be demethylated.

NMR, IR, MS

Analysis for $C_{29}H_{30}ClNO_5$: Theory: C, 68.57; H, 5.95; N, 2.76. Found: C, 67.28; H, 6.13; N, 2.66.

Example 13

Synthesis of 2-(4-hydroxyphenyl)-3-[4-[2-(piperidin-1-yl)ethoxy]benzoyl]-6-hydroxybenzofuran hydrochloride

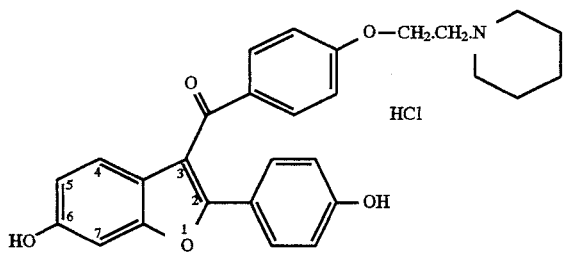

The title compound was prepared by dissolving the compound of Example 2, 2-(4-hydroxyphenyl)-3-[4-[2-(piperidin-1-yl)ethoxy]benzoyl]-6-hydroxybenzofuran, (3.1 g, 6.8 mmoles) in 15 ml of methanol and treating with an excess of 3% hydrochloric acid in methanol. The volume was then reduced by boiling to 15 ml. Warm water (20 ml) was then added and the reaction mixture was further warmed to clarify. The reaction mixture was then filtered, followed by gradual cooling to 0° C., at which temperature the mixture was maintained for about one hour. The crystals, which had precipitated, were collected by filtration and washed with cold water. The pale yellow crystals were dried overnight, resulting in 2.82 g (84%) of the desired title product. mp 213°–215° C.

NMR, IR, MS.

Analysis for $C_{28}H_{28}NO_5Cl$: Theory: C, 68.08; H, 5.71; N, 2.84; O, 16.19. Found: C, 67.86; H, 5.51; N, 2.88; O, 15.93.

Example 14

Synthesis of 2-(4-hydroxyphenyl)-3-[4-[2-(piperidin-1-yl)ethoxy]benzoyl]benzofuran hydrochloride

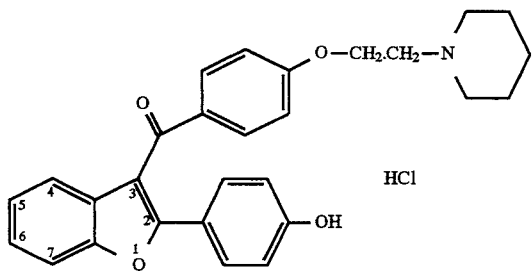

The 2-(4-hydroxyphenyl)-3-[4-[2-(piperidin-1-yl)ethoxy]benzoyl]benzofuran was prepared essentially as described in Example 2, except that phenol was used as a starting material in the synthesis described in Preparation 2 instead of 3-methoxy phenol. The hydrochloride salt of this substituted benzofuran was prepared essentially as described in Example 13, supra.

NMR, IR, MS.

Analysis for $C_{28}H_{28}NO_4Cl$: Theory: C, 70.36; H, 5.91; N, 2.93. Found: C, 70.46; H, 5.84; N, 2.84.

Example 15

Synthesis of 2-phenyl-3-[4-[2-(piperidin-1-yl)ethoxy]benzoyl]-6-hydroxybenzofuran hydrochloride

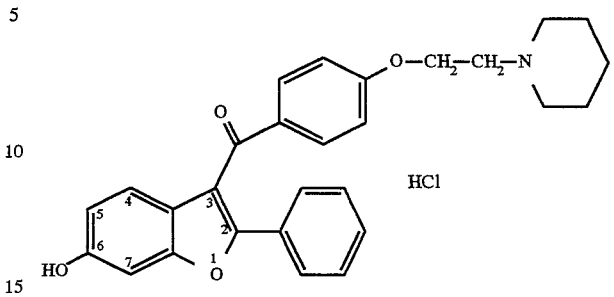

The 2-phenyl-3-[4-[2-(piperidin-1-yl)ethoxy]benzoyl]-6-hydroxybenzofuran was prepared essentially as described in Example 2, except that phenacylbromide (also known as α-bromoacetophenone) was used as a starting material in the synthesis described in Preparation 1 instead of 4-methoxyphenacylbromide. The hydrochloride salt of this substituted benzofuran was prepared essentially as described in Example 13, supra.

NMR, IR, MS.

Analysis for $C_{28}H_{28}NO_4Cl$: Theory: C, 70.36; H, 5.90; N, 2.93. Found: C, 70.39; H, 6.01; N, 2.91.

Example 16

Synthesis of 1-ethyl-2-(4-methoxyphenyl)-3-[4-[2-(piperidin-1-yl)ethoxy]benzoyl]-6-hydroxyindole hydrochloride salt

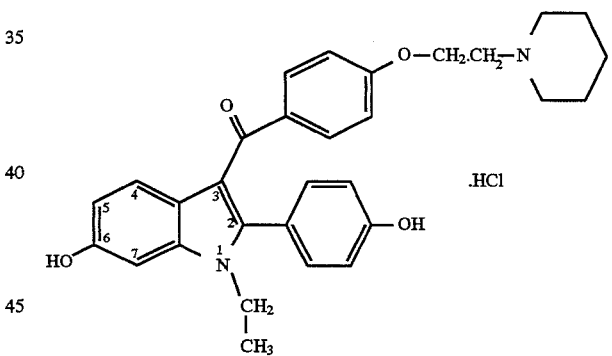

To 814 milliliters of concentrated hydrochloric acid in a 3 liter, 3-neck round bottom flask which had been cooled to 0° C. was added 3-methoxyaniline (99.26 g, 0.806 mole). Sodium nitrate (55.61 g, 0.806 mole), dissolved in 249 milliliters of water, was added dropwise to the 3-methoxyaniline solution at such a rate that the reaction temperature never exceeded 0° C. This mixture was then stirred for about 90 minutes.

Stannous chloride (545.57 g, 2.418 moles), dissolved in 497 milliliters of concentrated hydrochloric acid, was added dropwise to the reaction mixture at such a rate that the reaction temperature never exceeded 5° C. This mixture was then stirred for about two hours after the addition of the stannous chloride was completed, resulting in the formation of a thick, beige, chalky emulsion. The solid was removed by filtration, stored overnight in one liter of water and then basified with a 25% solution of sodium hydroxide. This aqueous solution was extracted with diethyl ether (3×1 liter) and then dried over sodium sulfate. The solvents were removed in vacuo, resulting in a brown oil of 3-methoxyphenylhydrazine (76.3 g, 69% yield).

The 3-methoxyphenylhydrazine (76.3 g, 0.552 mole) prepared supra, was dissolved in 400 milliliters of ethanol. To this mixture was added p-methoxyacetophenone (82.80 g, 0.552 mole) followed by the addition of about 6 drops of hydrochloric acid. This mixture was then stirred for about seven hours under a nitrogen atmosphere, followed by storage at 4° C. for about 3 days.

The white solid was then removed from the suspension by filtration under vacuum and then dried in vacuo, resulting in 135.2 grams (91% yield) of [(3-methoxyphenyl)hydrazono]-1-methyl-4-methoxybenzylidene of the following formula as a pale gray solid.

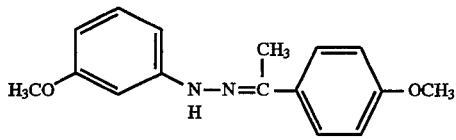

Zinc chloride (66.5 g, 0.49 mole) was added to a 3-neck round bottom flask under a nitrogen atmosphere. The flask and its contents were then heated to 200° C. at which time the hydrazone (26.4 g, 0.098 mole) prepared supra was added. The mixture was stirred for about 17 minutes, resulting in the formation of a brown tar and the evolution of some gas. The brown tar was then poured into two liters of 0.075N hydrochloric acid and this mixture was stirred for about 48 hours, resulting in the formation of a yellow solid.

The solids were removed by filtration and were then recrystallized from methanol. The solids were again removed by filtration and the solvents were removed in vacuo to yield the desired 2-(4-methoxyphenyl)-6-methoxyindole (5.50 g, 22% yield) as a white crystalline product.

The 2-(4-methoxyphenyl)-6-methoxyindole (2.0 g, 8 mmoles) was dissolved in 40 milliliters of N,N-dimethylformamide. This solution was added dropwise to a solution of sodium hydride (0.48 g, 12 mmoles) in ten milliliters of N,N-dimethylformamide. This reaction mixture was then stirred at room temperature for 1 hour at which time a solution of ethyl iodide (1.9 g, 12 mmoles) in N,N-dimethylformamide (10 mls) was added dropwise over five minutes. This mixture was then stirred at room temperature for about two hours.

The reaction was quenched by the addition of methanol. The volume of the solvents was reduced by vacuum, leaving a brown oil. This oil was diluted with chloroform, washed with 5N sodium hydroxide (3×75 ml), followed by washing with water (2×200 ml). The organic layer was dried over sodium sulfate and the solvents were removed in vacuo leaving 2.3 g of the desired intermediate 1-ethyl-2-(4-methoxyphenyl)-6-methoxyindole as white crystals.

The preceding intermediate was acylated at the 3-position by first placing N,N-dimethyl-4-methoxybenzamide (1.43 g, 8 mmoles), in a 100 ml flask cooled to 0° C. To this was then added phosphorous oxychloride (6.1 g, 40 mmoles) dropwise at such a rate that the reaction temperature never exceeded 20° C. The reaction mixture was allowed to warm to room temperature and was stirred for about 30 minutes. The reaction mixture was then cooled to 0° C. and the 1-ethyl-2-(4-methoxyphenyl)-6-methoxyindole (1.5 g, 5.33 moles) prepared supra, was added and the reaction mixture was then heated to 75° C. and maintained at this temperature for about three hours.

After this incubation, the reaction mixture was poured over ice and diluted with water. The layers were separated and the organic phase was washed with water (150 ml). The organic layer was dried over sodium sulfate and the solvents were removed in vacuo to yield a dark brown/black oil. This oil was taken up in 50 milliliters of methanol and cooled to 0° C. This solution was then basified by the dropwise addition of 2N sodium hydroxide (50 ml). The mixture was then heated to reflux for about 5 minutes, then cooled overnight at 4° C.

The precipitate was then removed by filtration and recrystallized from methanol, resulting in 2.21 grams (86% yield) of the intermediate 1-ethyl-2-(4-methoxyphenyl)-3-(4-methoxybenzoyl)-6-methoxyindole as a yellow precipitate.

The above intermediate (2.1 g, 5.05 mmoles) was then admixed with sodium thioethoxide (0.85 g, 10.11 mmoles) in N,N-dimethylformamide (12 mls). The reaction mixture was then heated to 85° C. and maintained at this temperature for about six hours. The desired intermediate 1-ethyl-2-(4-methoxyphenyl)-3-(4-hydroxybenzoyl)-6-methoxyindole was then recrystallized from ethyl acetate.

This intermediate (1.5 g, 3.74 mmoles) was then reacted with 2-(piperidin-1-yl)ethyl chloride hydrochloride (1.38 g, 7.5 mmoles) in N,N-dimethylformamide (60 mls) in the presence of cesium carbonate (3.26 g, 10 mmoles). This admixture was heated to 80° C. and maintained at this temperature for about two hours.

The precipitate was collected by filtration and then taken up in chloroform, and washed with 2N sodium hydroxide (3×125 ml) and water (3×100 ml). The organic fraction was then dried over sodium sulfate and the solvents were removed in vacuo to yield 2.05 grams (95% yield) of 1-ethyl-2-(4-methoxyphenyl)-3-[4-[2-(piperidin-1-yl)ethoxy]benzoyl]-6-methoxyindole as a gray foam.

This intermediate (1.0 g, 1.82 mmoles) was dissolved in dichloromethane (10 mls) and cooled to 0° C. To this mixture was then added the Lewis acid aluminum chloride (1.2 g, 9 mmoles) and the reaction mixture was then stirred for five minutes. Ethanol (3 mls) were then added and the reaction mixture was stirred on ice for about 15 minutes. The temperature of the reaction mixture was slowly raised to reflux and maintained at reflux for about 1.5 hours.

The reaction mixture was then cooled to 0° C. and this temperature was maintained as tetrahydrofuran (5 mls) was added. To this mixture was then added 20% hydrochloric acid in water (5 mls) and the reaction mixture was cooled back to 0° C. at which time five milliliters of water was then added, resulting in the formation of a yellow gum. This suspension was then placed at −40° C. and kept at this temperature for about 48 hours, after which time a grayish material was removed from the mixture by filtration. Thin layer chromatography confirmed this precipitate as the desired title product.

NMR, MS.

Analysis for $C_{30}H_{33}ClN_2O_4$: Theory: C, 69.15; H, 6.38; N, 5.38. Found: C, 69.09; H, 6.43; N, 5.53.

Example 17

Synthesis of 2-(4-hydroxyphenyl)-3-[4-[3-(piperidin-1-yl)propoxy]benzoyl]-6-hydroxybenzo[b]thiophene hydrochloride

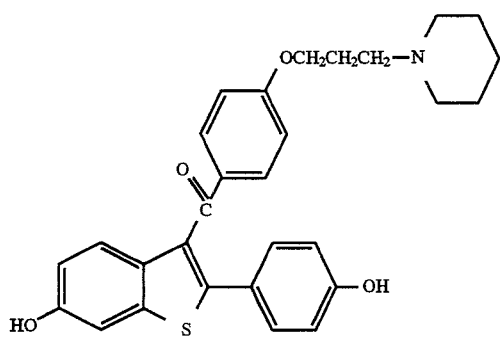

The title compound was prepared essentially as described in U.S. Pat. No. 4,380,635, which is herein incorporated by reference with the exception that 4-[3-(piperidin-1-yl)propoxy]benzoyl chloride was used to acylate the substituted benzo[b]thiophene rather than the 4-[2-(piperidin-1-yl)ethoxy]benzoyl chloride employed therein.

Example 18

Synthesis of 2-phenyl-3-[4-[2-(pyrrolidin-1-yl)ethoxy]benzoyl]benzo[b]thiophene

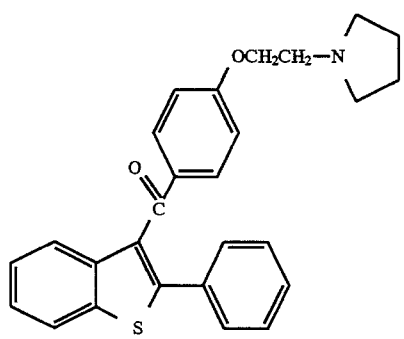

The title compound was prepared as described in U.S. Pat. No. 4,133,814, which is herein incorporated by reference.

Example 19

Synthesis of 2-phenyl-3-[4-[2-(pyrrolidin-1-yl)ethoxy]benzoyl]-6-methoxybenzo[b]thiophene citrate

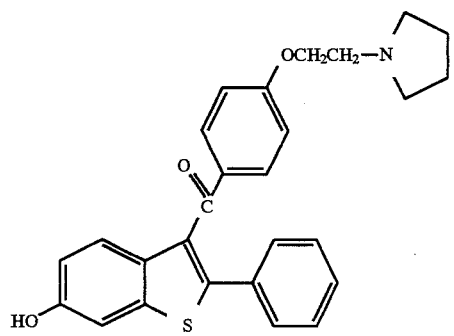

The title compound was prepared as described in U.S. Pat. No. 4,133,814, which is herein incorporated by reference.

Example 20

Synthesis of 2-(4-methoxyphenyl)-3-[4-[2-(pyrrolidin-1-yl)ethoxy]benzoyl]benzo[b]thiophene citrate

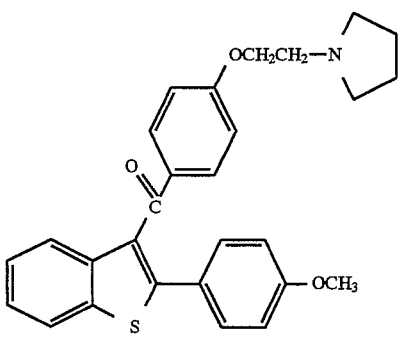

The title compound was prepared as described in U.S. Patent No. 4,133,814, which is herein incorporated by reference.

Example 21

Synthesis of 2-(4-ethoxyphenyl)-3-[4-[2-(pyrrolidin-1-yl)ethoxy]benzoyl]-6-methoxybenzo[b]thiophene citrate

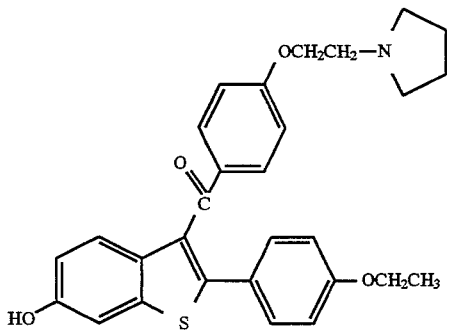

The title compound was prepared as described in U.S. Pat. No. 4,133,814, which is herein incorporated by reference.

Example 22

Synthesis of 2-(4-acetoxyphenyl)-3-[4-[2-(pyrrolidin-1-yl)ethoxy]benzoyl]benzo[b]thiophene citrate

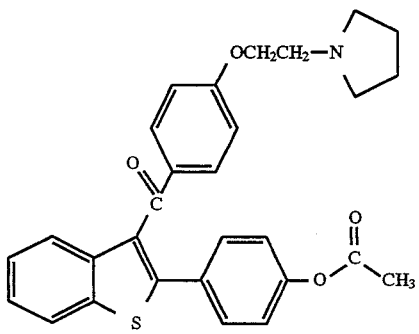

The title compound was prepared as described in U.S. Pat. No. 4,133,814, which is herein incorporated by reference.

Example 23

Synthesis of 2-phenyl-3-[4-[2-(piperidin-1-yl)ethoxy] benzoyl]benzo[b]thiophene

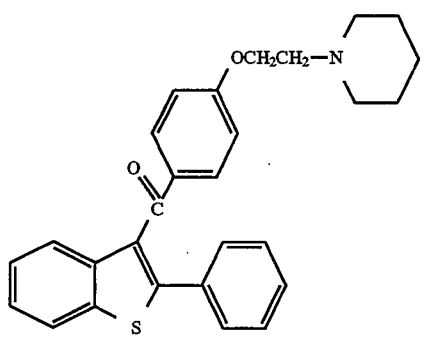

The title compound was prepared as described in U.S. Pat. No. 4,133,814, which is herein incorporated by reference.

Example 24

Synthesis of 2-phenyl-3-[4-[2-(piperidin-1-yl)ethoxy] benzoyl]-6-methoxybenzo[b]thiophene citrate

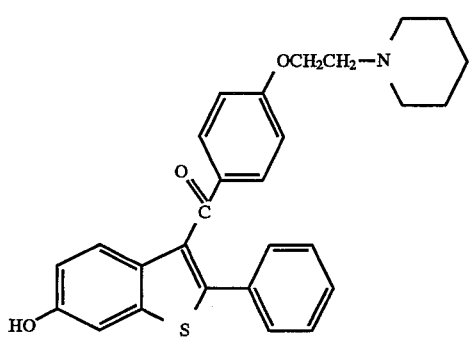

The title compound was prepared as described in U.S. Pat. No. 4,133,814, which is herein incorporated by reference.

Example 25

Synthesis of 2-(4-methoxyphenyl)-3-[4-[2-(piperidin-1-yl) ethoxy]benzoyl]benzo[b]thiophene citrate

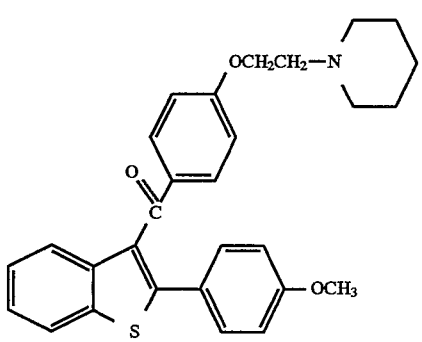

The title compound was prepared as described in U.S. Pat. No. 4,133,814, which is herein incorporated by reference.

Example 26

Synthesis of 2-(4-ethoxyphenyl)-3-[4-[2-(piperidin-1-yl) ethoxy]benzoyl]-6-methoxybenzo[b]thiophene citrate

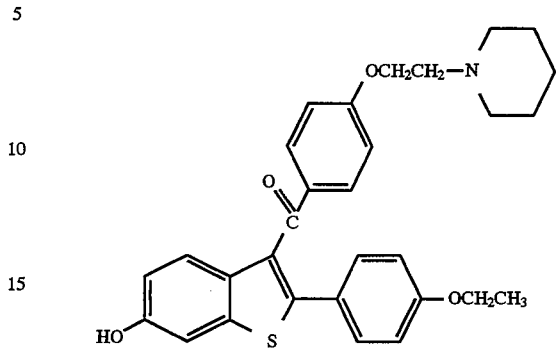

The title compound was prepared as described in U.S. Pat. No. 4,133,814, which is herein incorporated by reference.

Example 27

Synthesis of 2-(4-acetoxyphenyl)-3-[4-[2-(piperidin-1-yl) ethoxy]benzoyl]benzo[b]thiophene citrate

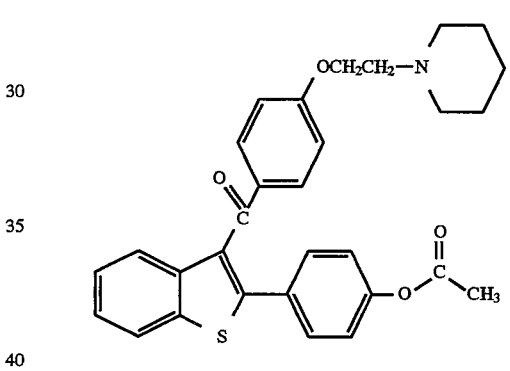

The title compound was prepared as described in U.S. Pat. No. 4,133,814, which is herein incorporated by reference.

Example 28

Synthesis of 2-(4-pentanoylphenyl)-3-[4-[2-(piperidin-1-yl) ethoxy]benzoyl]benzo[b]thiophene citrate

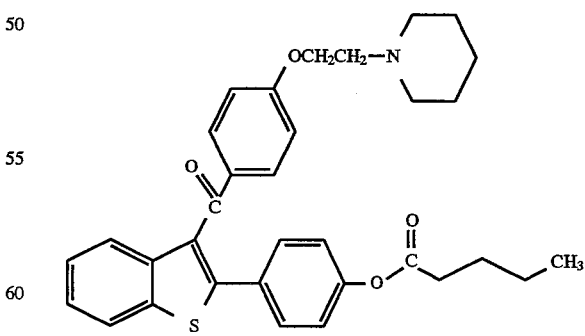

The title compound, also known as 2-(4-valerylphenyl)-3-[4-[2-(piperidin-1-yl)ethoxy]benzoyl]benzo[b]thiophene citrate, was prepared as described in U.S. Pat. No. 4,133,814, which is herein incorporated by reference.

Example 29

Synthesis of 2-(4-chlorophenyl)-3-[4-[2-(piperidin-1-yl)ethoxy]benzoyl]benzo[b]thiophene citrate

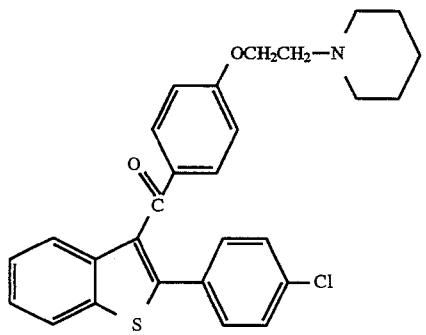

The title compound was prepared as described in U.S. Pat. No. 4,133,814, which is herein incorporated by reference.

Example 30

Synthesis of 2-phenyl-3-[4-[2-(hexamethyleneimin-1-yl)ethoxy]benzoyl]benzo[b]thiophene

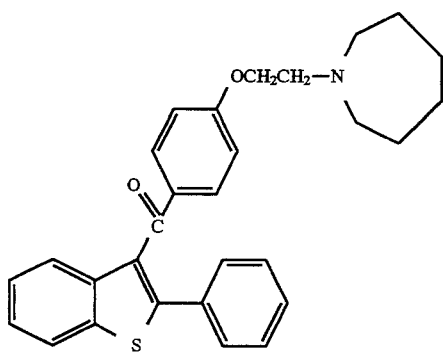

The title compound was prepared as described in U.S. Pat. No. 4,133,814, which is herein incorporated by reference.

Example 31

Synthesis of 2-phenyl-3-[4-[2-(hexamethyleneimin-1-yl)ethoxy]benzoyl]-6-methoxybenzo[b]thiophene citrate

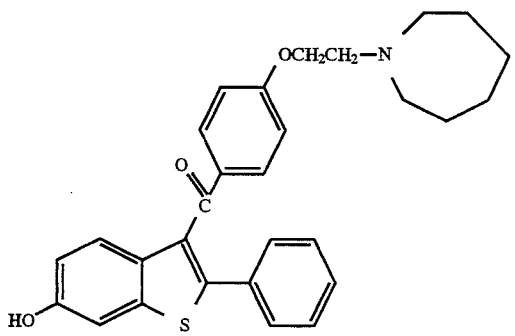

The title compound was prepared as described in U.S. Pat. No. 4,133,814, which is herein incorporated by reference.

Example 32

Synthesis of 2-(4-methoxyphenyl)-3-[4-[2-(hexamethyleneimin-1-yl)ethoxy]benzoyl]benzo[b]thiophene citrate

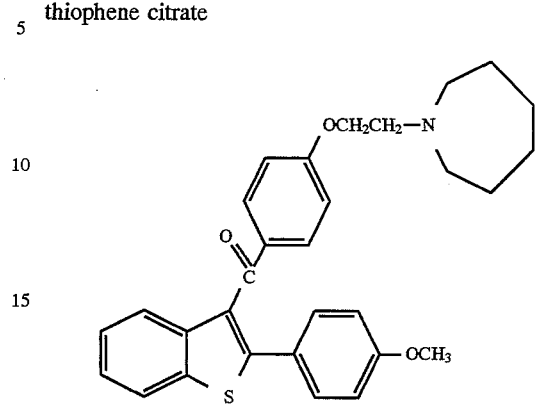

The title compound was prepared as described in U.S. Pat. No. 4,133,814, which is herein incorporated by reference.

Example 33

Synthesis of 2-(4-ethoxyphenyl)-3-[4-[2-(hexamethyleneimin-1-yl)ethoxy]benzoyl]-6-methoxybenzo[b]thiophene citrate

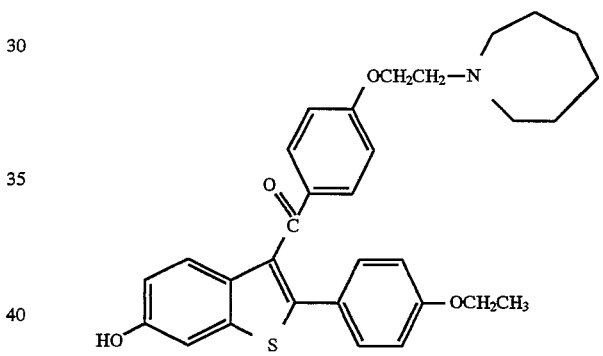

The title compound was prepared as described in U.S. Pat. No. 4,133,814, which is herein incorporated by reference.

Example 34

Synthesis of 2-(4-acetoxyphenyl)-3-[4-[2-(hexamethyleneimin-1-yl)ethoxy]benzoyl]benzo[b]thiophene citrate

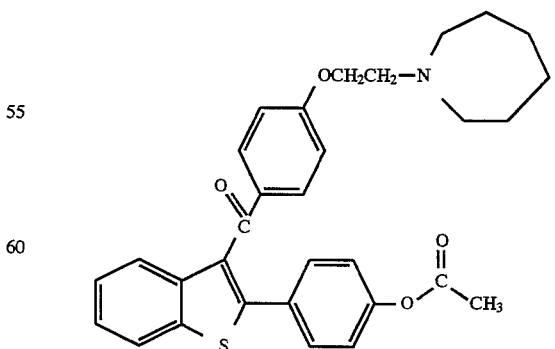

The title compound was prepared as described in U.S. Pat. No. 4,133,814, which is herein incorporated by reference.

Example 35

Synthesis of 2-(4-pentanoylphenyl)-3-[4-[2-(hexamethyleneimin-1-yl)ethoxy]benzoyl]benzo[b]thiophene citrate

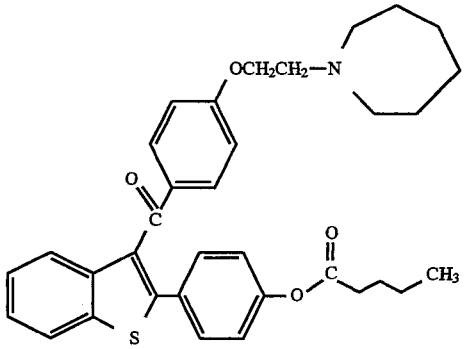

The title compound, also known as 2-(4-valerylphenyl)-3-[4-[2-(hexamethyleneimin-1-yl)ethoxy]benzoyl]benzo[b]thiophene citrate, was prepared as described in U.S. Pat. No. 4,133,814, which is herein incorporated by reference.

Example 36

Synthesis of 2-(4-chlorophenyl)-3-[4-[2-(hexamethyleneimin-1-yl)ethoxy]benzoyl]benzo[b]thiophene citrate

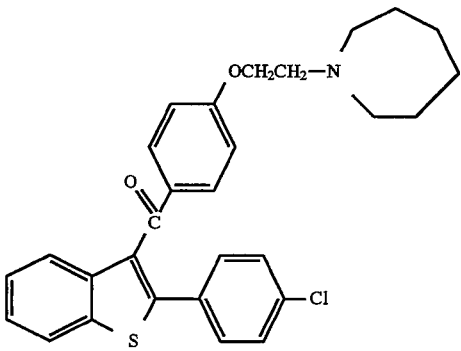

The title compound was prepared as described in U.S. Pat. No. 4,133,814, which is herein incorporated by reference.

Example 37

Synthesis of 2-(4-chlorophenyl)-3-[4-[2-(piperidin-1-yl)ethoxy]benzoyl]benzo[b]thiophene-1-oxide

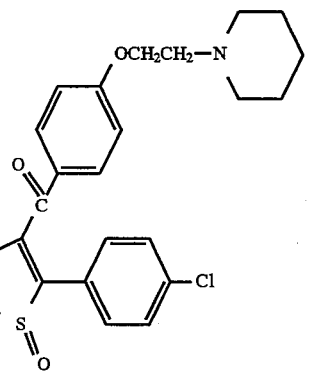

The title compound was prepared as described in U.S. Pat. No. 4,133,814, which is herein incorporated by reference.

Example 38

Synthesis of 2-(4-chlorophenyl)-3-[4-[2-(pyrrolidin-1-yl)ethoxy]benzoyl]benzo[b]thiophene-1-oxide

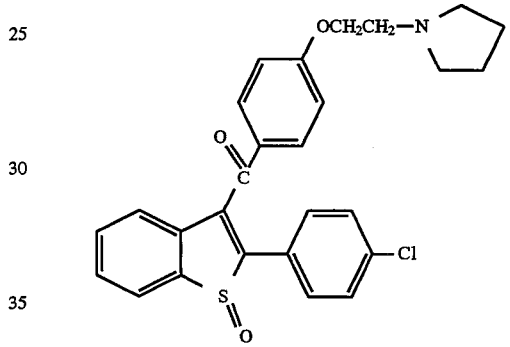

The title compound was prepared as described in U.S. Pat. No. 4,133,814, which is herein incorporated by reference.

The title compound was prepared as described in U.S. Pat. No. 4,133,814, which is herein incorporated by reference.

The compounds of the present invention bind to receptors specific for neuropeptide Y as well as the closely related neuropeptides. [For a review of neuropeptide Y receptors, see, D. Gehlert, Life Sciences, 55:551–562 (1994)]. Receptors for neuropeptide Y and peptide YY have considerable overlap while pancreatic polypeptide appears to have its own distinct set of receptors. Many, but not all, of the effects of neuropeptide Y can be replicated using peptide YY.

Two subtypes of receptors for neuropeptide Y were initially proposed on the basis of the affinity of the 13–36 fragment of neuropeptide Y using a preparation of the sympathetic nervous system. While these are the best established receptors for neuropeptide Y, a substantial body of evidence exists that there are additional receptor subtypes. The best established is a Y-3 receptor that is responsive to neuropeptide Y, but not to peptide YY. Another recently delineated receptor has been described that binds peptide YY with high affinity and neuropeptide Y with lower affinity. While the pharmacology of the feeding response to neuropeptide Y appears to be Y-1 in nature, a separate "feeding receptor" has been proposed. The Y-1 receptor is the only one that has been successfully cloned to date. The following paragraphs summarize the available information on the known neuropeptide Y receptor subtypes and their potential role in physiological function.

Y-1 Receptor

The Y-1 receptor is the best characterized receptor for neuropeptide Y. This receptor is generally considered to be postsynaptic and mediates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity. C. Wahlestedt, et al., *Regulatory Peptides*, 13:307-318 (1986); C. Wahlestedt, et al., NEURONAL MESSENGERS IN VASCULAR FUNCTION, 231-241 (Nobin, et al., eds. 1987). Substitution of the amino acid at position 34 with a proline (Pro$^{34}$) results in a protein which is specific for the Y-1 receptor. E. K. Potter, et al., *European Journal of Pharmacology*, 193:15-19 (1991). This tool has been used to establish a role for the Y-1 receptor in a variety of functions. The receptor is thought to be coupled to adenylate cyclase in an inhibitory manner in cerebral cortex, vascular smooth muscle cells, and SK-N-MC. [For a review, see, B. J. McDermott, et al., *Cardiovascular Research*, 27:893-905 (1993)]. This action is prevented by application of pertussis toxin confirming the role of a G-protein coupled receptor. The Y-1 receptor mediates the mobilization of intracellular calcium in a porcine vascular smooth muscle cells and human erythroleukemia cells.

The cloned human Y-1 receptor can couple to either phosphotidylinositol hydrolysis or the inhibition of adenylate cyclase, depending on the type of cell in which the receptor is expressed. H. Herzog, et al., *Proceedings of the National Academy of Sciences (USA)*, 89:5794-5798 (1992). The Y-1 receptor has been reported to couple to either second messenger system when studied using tissue preparations or cell lines naturally expressing te receptor. D. Gehlert, supra, at 553. The Y-1 receptor cannot, therefore, be distinguished solely on the basis of coupling to a single second messenger.

Y-2 Receptor

As with the Y-1 receptor, this receptor subtype was first delineated using vascular preparations. Pharmacologically, the Y-2 receptor is distinguished from Y-1 by exhibiting affinity for C-terminal fragments of neuropeptide Y. The receptor is most often differentiated by the use of neuropeptide Y(13-36), though the 3-36 fragment of neuropeptide Y and peptide YY provides improved affinity and selectivity. Y. Dumont, et al., *Society for Neuroscience Abstracts*, 19:726 (1993). Like Y-1 receptor, this receptor is coupled to the inhibition of adenylate cyclase, though in some preparations it may not be sensitive to pertussis toxin. The Y-2 receptor was found to reduce te intracellular levels of calcium in the synspse by selective inhibition of N-type calcium channels. Like the Y-1 receptor, te Y-2 receptor may exhibit differential coupling to second messengers.

The Y-2 receptors are found in a variety of brain regions, including the hippocampus, substantia nigralateralis, thalamus, hypothalamus, and brainstem. In the periphery, Y-2 is found in the peripheral nervous system, such as sympathetic, parasympathetic, and sensory neurons. In all these tissues, Y-2 receptors mediate a decrease in the release of neurotransmitters.

Y-3 Receptor

This receptor is the newest and least studied of the established neuropeptide Y receptor subtypes. While neuropeptide Y is a fully efficacious agonist at this receptor population, peptide YY is weakly efficacious. This pharmacological property is used to define this receptor. A receptor that has similar pharmacology to the Y-3 receptor has been identified in the CA3 region of the hippocampus using electrophysiological techniques. This receptor may potentiate the excitatory response of these neurons to N-methyl-D-aspartate (NMDA). F. P. Monnet, et al., *European Journal of Pharmacology*, 182:207-208 (1990).

The presence of this receptor is best established in the rat brainstem, specifically in the nucleus tractus solitarius. Application of neuropeptide Y to this region produces a dose-dependent reduction in blood pressure and heart rate. This area of the brain also may have significant contributions from the Y-1 and Y-2 receptor. Neuropeptide Y also inhibits the acetylcholine-induced release of catecholamines from the adrenal medulla, presumably through a Y-3 receptor. C. Wahlestedt, et al., *Life Sciences*, 50:PL7-PL14 (1992).

Peptide YY Preferring Receptor

A fourth receptor has been described that exhibits a modest preference for peptide YY over neuropeptide Y. This receptor was first described in the rat small intestine as having a 5-10 fold higher affinity for peptide YY over neuropeptide Y. M. Laburthe, et al., *Endocrinology*, 118:1910-1917 (1986). Subsequently, this receptor was found in the adipocyte and a kidney proximal tubule cell line. This receptor is coupled in an inhibitory manner to adenylate cyclase and is sensitive to pertussis toxin.

In the intestine, this receptor produces a potent inhibition of fluid and electrolyte secretion. The receptor is localized to te crypt cells where intestinal chloride secretion is believed to take place. The peptide YY preferring receptor in adipocytes mediates a reduction in lipolysis by way of a cyclic adenosine monophosphate (cAMP)-dependent mechanism.

"Feeding Receptor"

One of the earliest discovered central effects of neuropeptide Y was a profound increase in food intake that was observed following the hypothalmic administration of the peptide to rats. The response was greatest when the peptide was infused into the perifornical region of the hypothalamus. B. G. Stanley, et al., *Brain Research*, 604:304-317 (1993). While the pharmacology of this response resembled the Y-1 receptor, the 2-36 fragment of neuropeptide Y was significantly more potent than neuropeptide Y. In addition, intracerebroventricular neuropeptide Y(2-36) fully stimulates feeding, but does not reduce body temperature as does full length neuropeptide Y. F. B. Jolicoeur, et al., *Brain Research Bulletin*, 26:309-311 (1991).

The biological activity of the compounds of the present invention was evaluated employing an initial screening assay which rapidly and accurately measured the binding of the tested compound to known neuropeptide Y receptor sites. Assays useful for evaluating neuropeptide Y receptor antagonists are well known in the art. See,. e.g., U.S. Pat. No. 5,284,839, issued Feb. 8, 1994, which is herein incorporated by reference. See also, M. W. Walker, et al., *Journal of Neurosciences*, 8:2438-2446 (1988).

Neuropeptide Y Binding Assay

The ability of the compounds of the instant invention were assessed as to their ability to bind to neuropeptide Y using a protocol essentially as described in M. W. Walker, et al., supra. In this assay the cell line SK-N-MC was employed. This cell line was received from Sloane-Kettering Memorial Hospital, New York. These cells were cultured in T-150 flasks using Dulbecco's Minimal Essential Media (DMEM) supplemented with 5% fetal calf serum. The cells were manually removed from the flasks by scraping, pelleted, and stored at −70° C.

The pellets were resuspended using a glass homogenizer in 25 mM HEPES (pH 7.4) buffer containing 2.5 mM calcium chloride, 1 mM magnesium chloride, and 2 g/L bacitracin. Incubations were performed in a final volume of 200 μl containing 0.1 nM $^{125}$I-peptide YY (2200 Ci/mmol) and 0.2–0.4 mg protein for about two hours at room temperature.

Nonspecific binding was defined as the amount of radioactivity remaining bound to the tissue after incubating in the presence of 1 μM neuropeptide Y. In some experiments various concentrations of compounds were included in the incubation mixture.

Incubations were terminated by rapid filtration through glass fiber filters which had been presoaked in 0.3% polyethyleneimine using a 96-well harvester. The filters were washed with 5 ml of 50 mM Tris (pH 7.4) at 4° C. and rapidly dried at 60° C. The filters were then treated with melt-on scintillation sheets and the radioactivity retained on the filters were counted. The results were analyzed using various software packages. Protein concentrations were measured using standard coumassie protein assay reagents using bovine serum albumin as standards.

Many of the compounds prepared supra showed significant activity as neuropeptide Y receptor antagonists. As the compounds of Formula I are effective neuropeptide Y receptor antagonists, these compounds are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders may include:

- disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;
- conditions related to increased sympathetic nerve activity for example, during or after coronary artery surgery, and operations and surgery in the gastrointestinal tract;
- cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;
- conditions related to pain or nociception;
- diseases related to abnormal gastrointestinal motility and secretion, such as different forms of ileus, urinary incontinence, and Crohn's disease;
- abnormal drink and food intake disorders, such as obesity, anorexia, bulimia, and metabolic disorders;
- diseases related to sexual dysfunction and reproductive disorders;
- conditions or disorders associated with inflammation;
- respiratory diseases, such as asthma and conditions related to asthma and bronchoconstriction; and
- diseases related to abnormal hormone release, such as leutinizing hormone, growth hormone, insulin, and prolactin.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid compositions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dipsersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compositions may be administered, preferably orally or nasally, from devices which deliver the formulation in an appropriate manner.

The following examples illustrate the pharmaceutical compositions of the present invention.

Formulation Preparation 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient | 250.0 mg |
| Isotonic saline | 1000 ml |

Formulation Preparation 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method for the treatment of a physiological disorder associated with an excess of neuropeptide Y, which method comprises administering to a mammal in need of said treatment an effective amount of a compound of the formula

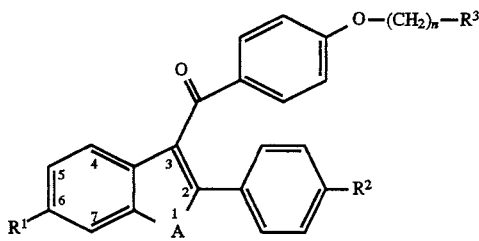

wherein:

A is —O—, —S(O)$_m$—, or —N(R$^{11}$)—;
where R$^{11}$ is hydrogen or C$_1$–C$_6$ alkyl, and m is 0, 1, or 2;

R$^1$ is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, or trifluoromethyl;

R$^2$ is hydroxy, halo, hydrogen, C$_3$–C$_8$ cycloalkyl, C$_2$–C$_7$ alkanoyloxy, C$_1$–C$_6$ alkoxy, or phenyl, said phenyl being optionally substituted with one, two, or three moieties selected from the group consisting of C$_1$–C$_4$ alkyl, C$_1$–C$_4$ alkoxy, nitro, chloro, fluoro, or trifluoromethyl;

n is 1–6;

R$^3$ is a group of the formula

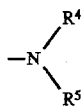

wherein R$^4$ and R$^5$ are independently C$_1$–C$_6$ alkyl or combine to form, along with the nitrogen to which they are attached, a heterocyclic ring selected from the group consisting of hexamethyleneiminyl, piperazinyl, heptamethyleneiminyl, imidazolinyl, piperidinyl, 4-methylpiperidinyl, pyrrolidinyl, or morpholinyl;

with the proviso that when n is 2 and A is —S—, both R$^1$ and R$^2$ are not both selected from the group consisting of hydroxy, methoxy, and C$_2$–C$_7$ alkanoyloxy;

or a pharmaceutically acceptable salt thereof.

2. A method as claimed in claim 1 employing a compound wherein at least one of R$^1$ and R$^2$ is hydroxy.

3. A method as claimed in claim 2 employing a compound wherein A is —O—.

4. A method as claimed in claim 2 employing 2-(4-hydroxyphenyl)-3-[4-[2-(hexamethyleneimin-1-yl)ethoxy]benzoyl]-6-hydroxybenzofuran, 2-(4-hydroxyphenyl)-3-[4-[2-(piperidin-1-yl)ethoxy]benzoyl]-6-hydroxybenzofuran, 2-(4-hydroxyphenyl)-3-[4-[2-(pyrrolidin-1-yl)ethoxy]benzoyl]-6-hydroxybenzofuran, 2-(4-hydroxyphenyl)-3-[4-[2-(N,N-diethylamino)ethoxy]benzoyl]-6-hydroxybenzofuran, 2-(4-hydroxyphenyl)-3-[4-[2-(N,N-diisopropylamino)ethoxy]benzoyl]-6-hydroxybenzofuran, or 2-(4-hydroxyphenyl)-3-[4-[2-(N,N-dimethylamino)ethoxy]benzoyl]-6-hydroxybenzofuran or a pharmaceutically acceptable salt or solvate thereof.

5. A method as claimed in claim 2 employing a compound wherein A is —S(O)$_m$—.

6. A method as claimed in claim 5 employing a compound wherein m is 0.

7. A method as claimed in claim 6 employing 2-(4-chlorophenyl)-3-[4-[2-(hexamethyleneimin-1-yl)ethoxy]benzoyl]-6-hydroxybenzo[b]thiophene, 2-(4-hydroxyphenyl)-3-[4-[2-(piperidin-1-yl)ethoxy]benzoyl]benzo[b]thiophene, 2-(4-hydroxyphenyl)-3-[4-[2-(pyrrolidin-1-yl)ethoxy]benzoyl]benzo[b]thiophene, 2-(4-hydroxyphenyl)-3-[4-[2-(N,N-diethylamino)ethoxy]benzoyl]benzo[b]thiophene, 2-(4-hydroxyphenyl)-3-[4-[2-(N,N-diisopropylamino)ethoxy]benzoyl]benzo[b]thiophene, or 2-(4-hydroxyphenyl)-3-[4-[2-(N,N-dimethylamino)ethoxy]benzoyl]benzo[b]thiophene or a pharmaceutically acceptable salt or solvate thereof.

8. A method as claimed in claim 2 employing a compound wherein A is —N(R$^{11}$)—.

9. A method as claimed in claim 8 employing 1-ethyl-2-(4-methoxyphenyl)-3-[4-[2-(piperidin-1-yl)ethoxy]benzoyl]-6-hydroxyindole or a pharmaceutically acceptable salt or solvate thereof.

10. A method as claimed in claim 1 employing a compound wherein at least one of R$^1$ and R$^2$ is methoxy.

11. A method as claimed in claim 10 employing a compound wherein A is —O—.

12. A method as claimed in claim 11 employing 2-(4-methoxyphenyl)-3-[4-[2-(hexamethyleneimin-1-yl)ethoxy]benzoyl]-6-methoxybenzofuran, 2-(4-methoxyphenyl)-3-[4-[2-(piperidin-1-yl)ethoxy]benzoyl]-6-methoxybenzofuran, 2-(4-methoxyphenyl)-3-[4-[2-(pyrrolidin-1-yl)ethoxy]benzoyl]-6-methoxybenzofuran, 2-(4-methoxyphenyl)-3-[4-[2-(N,N-diethylamino)ethoxy]benzoyl]-6-methoxybenzofuran, 2-(4-methoxyphenyl)-3-[4-[2-(N,N-diisopropylamino)ethoxy]benzoyl]-6-methoxybenzofuran, or 2-(4-methoxyphenyl)-3-[4-[2-(N,N-dimethylamino)ethoxy]benzoyl]-6-methoxybenzofuran or a pharmaceutically acceptable salt or solvate thereof.

13. A method as claimed in claim 10 employing a compound wherein A is —S(O)$_m$—.

14. A method as claimed in claim 13 employing a compound wherein m is 0.

15. A method as claimed in claim 14 employing 2-(4-methoxyphenyl)-3-[4-[3-(hexamethyleneimin-1-yl)propoxy]benzoyl]benzo[b]thiophene, 2-(4-methoxyphenyl)-3-[4-[2-(hexamethyleneimin-1-yl)ethoxy]benzoyl]benzo[b]thiophene, 2-(4-methoxyphenyl)-3-[4-[3-(piperidin-1-yl)propoxy]benzoyl]benzo[b]thiophene, 2-(4-methoxyphenyl)-3-[4-[2-(pyrrolidin-1-yl)ethoxy]benzoyl]benzo[b]thiophene, 2-(4-methoxyphenyl)-3-[4-[2-(N,N-diethylamino)ethoxy]benzoyl]benzo[b]thiophene, 2-(4-methoxyphenyl)-3-[4-[2-(N,N-diisopropylamino)ethoxy]

benzoyl]benzo[b]thiophene, or 2-(4-methoxyphenyl)-3-[4-[2-(N,N-dimethylamino)ethoxy]benzoyl]benzo[b]thiophene or a pharmaceutically acceptable salt or solvate thereof.

16. A method as claimed in claim 10 employing a compound wherein A is —N(R$^{11}$)—.

17. A method as claimed in claim 16 employing 1-ethyl-2-(4-methoxyphenyl)-3-[4-[2-(piperidin-1-yl)ethoxy]benzoyl]-6-methoxyindole or a pharmaceutically acceptable salt or solvate thereof.

18. A method as claimed in claim 1 wherein the physiological disorder associated with an excess of neuropeptide Y is selected from the group consisting of anxiety, depression, psychosis, and schizophrenia.

19. A method as claimed in claim 1 wherein the physiological disorder associated with an excess of neuropeptide Y is selected from the group consisting of dementia, Alzheimer's disease, Down's Syndrome, multiple sclerosis, cerebral stroke, and amyotrophic lateral sclerosis.

20. A method as claimed in claim 1 wherein the physiological disorder associated with an excess of neuropeptide Y is selected from the group consisting of adult respiratory distress syndrome, bronchopneumonia, bronchospasm, and asthma.

21. A method as claimed in claim 1 wherein the physiological disorder associated with an excess of neuropeptide Y is selected from the group consisting of urinary incontinence, irritable bowel syndrome, inflammatory bowel disease, psoriasis, fibrositis, osteoarthritis, and rheumatoid arthritis.

22. A method as claimed in claim 1 wherein the physiological disorder associated with an excess of neuropeptide Y is pain or nociception.

23. A method as claimed in claim 1 wherein the physiological disorder associated with an excess of neuropeptide Y is chronic pain, migraine, or post-operative pain.

* * * * *